United States Patent
Hunter (10) Patent No.: US 6,389,595 B1
(45) Date of Patent: May 21, 2002

(54) EYE SHADE

(76) Inventor: Kenneth Hunter, 8 Llwelyn Mansions, 127 Hammersmith Road, London (GB), W14OQR ( * ) Notice: Subject to any disclaimer, the term of this patent is extended or adjusted under 35 U.S.C. 154(b) by 0 days.

(21) Appl. No.: 09/510,920

(22) Filed: Feb. 22, 2000

Related U.S. Application Data (60) Provisional application No. 60/134,094, filed on May 14, 1999.

(51) Int. Cl.[7] ............................................. A61F 9/00
(52) U.S. Cl. .................................... 2/12; 351/155
(58) Field of Search ................. 2/6.3, 6.5, 10, 2/12, 13, 171, 171.8, 195.6, 195.7, 209.13, 424, DIG. 11, 452, 453, 454; 351/155; 128/858

(56) References Cited

U.S. PATENT DOCUMENTS

| | | | | |
|---|---|---|---|---|
| 2,449,303 A | * | 9/1948 | Laing | 2/12 |
| 2,462,258 A | * | 2/1949 | Dannenberg | 2/171 |
| 4,393,519 A | * | 7/1983 | Nicastro | 2/12 |
| 4,414,693 A | * | 11/1983 | Brody | 2/435 |
| 4,811,430 A | * | 3/1989 | Janusz | 2/452 |
| 4,852,189 A | * | 8/1989 | Duggan | 2/452 |
| 4,955,087 A | * | 9/1990 | Perez et al. | 2/12 |
| 5,105,475 A | * | 4/1992 | Lynd et al. | 2/10 |
| 5,303,423 A | * | 4/1994 | Gazzara et al. | 2/9 |
| 5,309,577 A | * | 5/1994 | Buononato et al. | 2/452 |
| 5,473,778 A | * | 12/1995 | Bell | 2/10 |
| 5,491,841 A | * | 2/1996 | Valletta | 2/10 |
| 5,581,807 A | * | 12/1996 | Peterson | 2/10 |
| 5,617,589 A | * | 4/1997 | Lacore et al. | 2/452 |
| 5,771,500 A | * | 6/1998 | Mayes | 2/452 |
| 5,930,834 A | * | 8/1999 | Toovey | 2/10 |
| 6,047,401 A | * | 4/2000 | Traumer | 2/10 |

* cited by examiner

*Primary Examiner*—John J. Calvert
*Assistant Examiner*—Katherine Moran
(74) *Attorney, Agent, or Firm*—Kenneth W. Float (57) ABSTRACT

A number of eye shades having a headband coupled to a transparent visor are disclosed. The visor extends downward from the headband so that it is positioned in front of a wearer's eyes when worn. The visor may have a resilient protective nosepiece attached thereto. The headband may be made of a flexible material that wraps around a top edge of the visor and is affixed thereto, such as by sewing or adhesive. The eye shade may be foldable including a foldable headband and vented end members that are attached to and fold behind the visor. The headband and visor may be attached to an interior surface of a hat to provide an item of headgear.

24 Claims, 7 Drawing Sheets

EYE SHADE

This application claims priority from provisional application Ser. No. 60/134,094, filed May 14, 1999.

BACKGROUND

The present invention relates generally to an eye shade, and more particularly to improved eye shades that may be worn on the forehead.

The eyes are, by nature, particularly sensitive organs and as such need to be carefully looked after. Exposure of the eyes to direct sunlight or indeed the reflected glare of sunlight can cause a variety of problems, ranging from simple discomfort to permanent damage. These are problems which are experienced by anybody who spends any length of time in the sun, this includes everybody from sportsmen to holiday-makers etc., and therefore the requirement for means which reduce the significance of these problems, is great. In some circumstances it may be necessary to protect the eyes from other sources of bright light.

Conventional means for protecting the eyes include tinted glasses, commonly referred to as sunglasses. The structure of a pair of sunglasses is such that they rest on the bridge of the nose and tops of the ears. The weight of the sunglasses on these points is noticeable and while they reduce the discomfort associated with direct sunlight, they may still be uncomfortable to the wearer. If the wearer also wishes to shade the crown of his head as well as shading his eyes, he must generally also wear a hat. This can further increase the discomfort experienced by the wear around the region of the tops of the ears.

In addition to sunglasses, items of headgear which incorporate means for shading the eyes such as a sun visor arrangement, have been developed. In general, the visor part of such headgear extends orthogonally, or near orthogonally to the plane of the wearer's face.

GM 2,102,670 discloses a visor construction whereby the visor part of the invention is fabricated into an open cell configuration. The plane at which the visor to designed to project is perpendicular to the forehead and hence can only shade the eyes of the wearer from certain directions.

SU 1,824,176 discloses a similar arrangement and is designed specifically for the driver of a vehicle. The visor of this invention is a solid barrier is split down the central line into two halves. The first half projects directly away from the forehead and is situated on the side of the headgear that is closest to the door of the vehicle. The second half of the visor is directed upwards, orthogonal to both the first section of the visor and to the forehead of the wearer.

One particular disadvantage of these types of visored headgear is that they only provide shading from the sun when the sun is above the plane of the visor. There is no provision included in the design of the headgear which shades the wearer from both direct sunlight and from reflected light and glare that approach the wearer from below the plane of the visor.

U.S. Pat. No. 4,192,017 details an example of visored headgear whereby the visor is removable and can be exchanged for different ones, displaying a differ logo, but the visor itself projects out from the forehead of the wearer at a slight downward angle. However, this angle is not sufficient to solve the above-mentioned problem.

The disclosure in U.S. Pat. No. 4,869,586 describes the use of an arrangement which allows the attachment of the lens portion of a pair of sunglasses to the peak of a cap. The lens arrangement is hinged along the top edge and thus can be placed in a shading position in front of the eyes or alternatively in a storage position when not required. As this invention does not allow for the shading of the eyes from sunlight from the side of the wearer, all round shading protection cannot be provided.

These examples of eye shades do not allow for efficient shading of the wearer from the sun, especially if the wearer tilts his head backwards or the sun is low in the sky. This may not only prove uncomfortable, but both detrimental to the health of the eyes of the wearer and, if sudden dazzling occurs, dangerous to the wearer. In addition, the visors of the prior art are fabricate from solid, non-transparent materials, and therefore the field of vision of the wearer is reduced.

Accordingly, it would be advantageous to have improved eye shades for shading of the wearer from the sun.

SUMMARY OF THE INVENTION

The present invention seeks to address the above and other problems. In general, the present invention can be differentiated from the prior art by virtue of the fact that key structural parameters have been determined to maximize the correlation between shading from the sun and comfort of the wearer.

According to the present invention, there is provided in the first aspect, an eye shade comprising a headband and a transparent visor member, the visor member extending downwardly from the headband such that when worn it is positioned in front of the wearer's eyes. In a particularly preferred arrangement, the visor member shaped such that it extends around the frontal region of the wearer's head. That is to say that the visor is of the "wrap around" type.

One advantage the present invention has over sunglasses is that the headband construction fits comfortably on the forehead, preferably extending around the circumference of the head and does not need to rest on any facial feature such as the nose or the tops of the ears. The fact that the downward angle of the visor member relative to the plane of the face is small has an advantage over conventional sun visor designs in that it helps provide all around shading from the sun and eliminates the risk that the wearer will be suddenly dazzled by the sun, yet retaining the maximum field of vision.

In one preferred arrangement the top edge of the visor member is spaced away from the forehead, this arrangement having the advantage that the main body of the visor sits comfortably away from facial features such as the eyebrows and the nose. As many people wear spectacles to correct defects in their vision, an arrangement in which the visor member sits away from the face is particularly advantageous as the spectacles may be worn in conjunction with the eye shade.

The spacing of the visor member from the forehead may be achieved by any suitable means. In a particularly preferred arrangement, the head band include a spacer member which is preferably comprised of a foamed material.

Of the possible embodiments of the invention, two are particularly preferred. The first comprises a basic headband construction incorporating a visor member that is positioned in front of the eyes of the wearer such that the wearer is shaded and in further arrangements, protected from the sun or other light source. The second embodiment comprises the essential features of the invention incorporated in the design of an item of headgear, or hat.

In a further alternative embodiment of the present invention, essential features of the eye shade are incorporated into the design of a hat allowing an alternate method of attachment to the head. The advantage of this feature is that total shading of both the eyes and the crown of the head may be achieved with the use of a single device and not the rather cumbersome combination of glasses and a form of headgear.

In another aspect of the present invention, thee is provided a hat that incorporates an eye shade as described before. Therefore, the features disclosed above may be included in their entirety or in combination, into the construction of an all-in-one visored headgear. These features have been found to give rise to a particularly effective form of eye shade.

Another embodiment of the present invention has a visor member preferably configured with a resilient protective nosepiece upon which the eye shade may rest on a wearer's nose without causing discomfort. This embodiment has a headband that wraps around the top edge of the visor member and is sewn or adhesively attached to the visor member. The headband may have a logo or other advertisement disposed on an exposed surface thereof. The logo or advertisement may be embroidered, stitched or otherwise affixed to the exposed surface of the headband. The headband may be provided with attachable ends that may be second together using various types of fasteners.

Yet another embodiment of the present invention provides for a foldable eye shade. In this embodiment, the visor member is preferably configured with the resilient protective nosepiece and distal ends of the visor member are secured to vented end members. The vented end members are made of a resilient material. The vented end members have a central mesh or screen that permits ventilation through the sides of the eye shade. The headband wraps around the top edge of the visor member and is sewn or adhesively attached to the visor member and the vented end members. The headband and the vented end members are bendable or foldable adjacent the respective distal ends of the visor member. The headband may be attached to an adjustable or stretchable material to allow the eye shade to be slipped over the top portion of the head to cover the eyes. Alternatively, the headband may be provided with attachable ends that are secured together using fasteners of various kinds.

BRIEF DESCRIPTION OF THE DRAWINGS

The various features and advantages of the present invention may be more readily understood with reference to the following detailed description taken in conjunction with the accompanying drawings, described by way of example, and wherein like reference numerals designate like structural elements, and in which.

DETAILED DESCRIPTION

Figure 1:
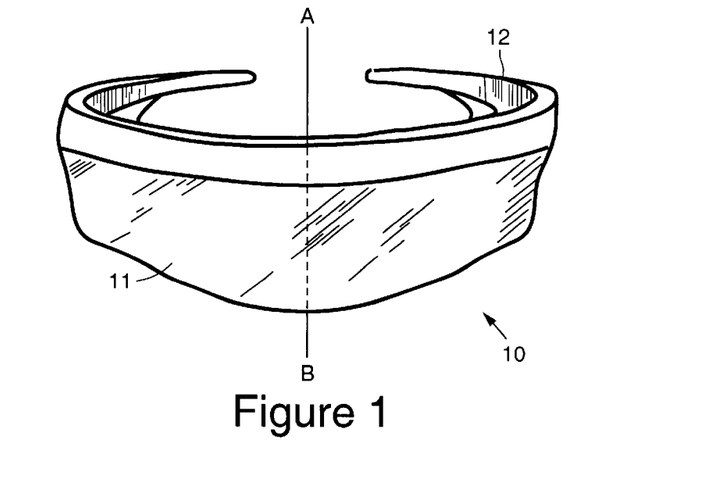
FIG. 1 a front perspective view of an exemplary eye shade in accordance with the principles of the present invention.

Referring to FIG. 1, the overall structure of a clip-style headband embodiment of an eye shade 10 in accordance with the principles of the present invention is shown, whereby a visor member 11 is embedded in a headband construction 12.

Figure 2:
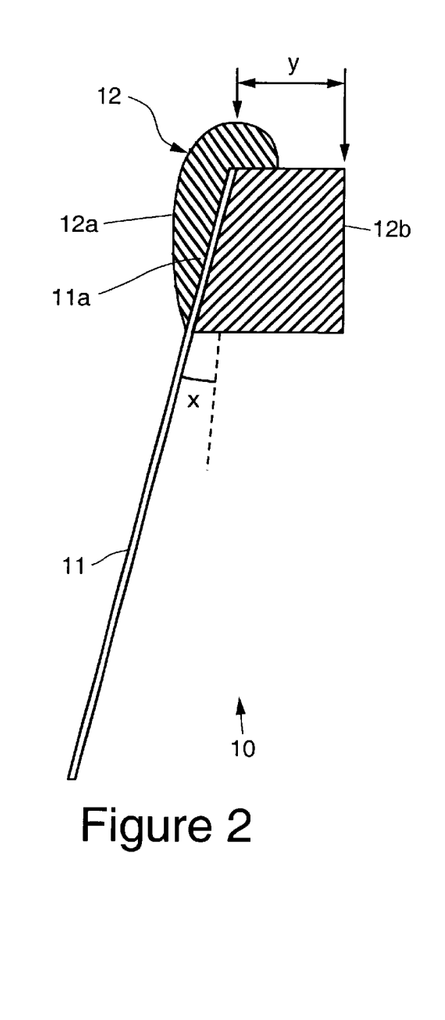
FIG. 2 as a schematic part cross-sectional diagram through the line AB depicted in FIG. 1.

FIG. 2 shows a cross-sectional view of the eye shade 10 through a section taken along the line AB shown in FIG. 1. In this particular arrangement, the headband construction 12 is comprised of three layers, including a headband 12a, a top part of the visor member 11a and a spacer member 12b. The structure of the headband construction 12 is defined by the two parameters "x" and "y", wherein x is the angle the visor member 11 is declined from the vertical for the plane of the face), measured in degrees and y is the distance the top edge of the visor member 11 is from the forehead of a wearer, measured in millimeters.

The visor member 11 is spaced from the forehead in order that facial features such as the nose and the eyebrows are accommodated. The angle at which the visor member 11 is declined (x), not only assists in ensuring that these facial features are indeed accommodated, but also provides for optimum all-around shading from the sun.

Figure 3:
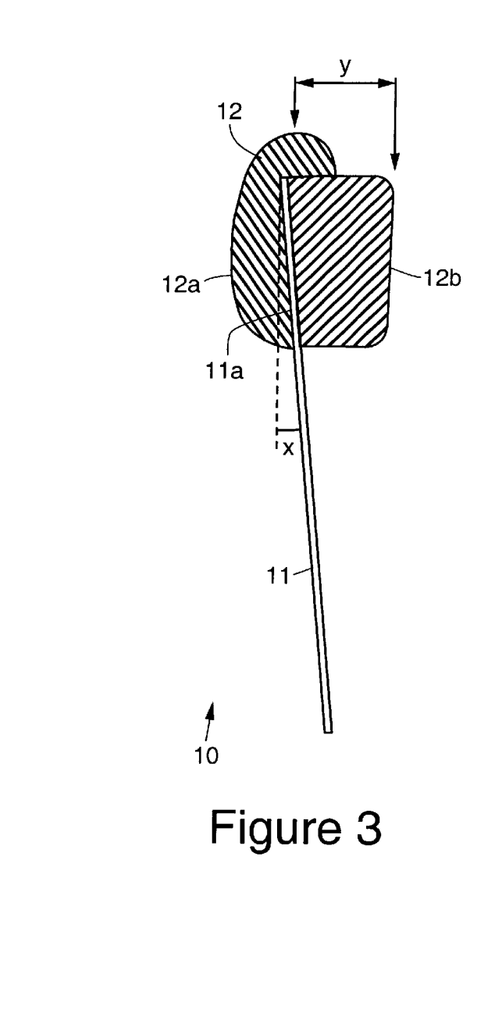
FIG. 3 is a schematic part cross-section diagram through the line AB depicted in an alternative arrangement of the eye shade shown in FIG. 1.

FIG. 3 depicts a cross-section of an alternative arrangement of the eye shade 10 through the section taken among the line AB shown in FIG. 1. As with the eye shade 10 illustrated in FIG. 2, the headband construction 12 is comprised of three layers, including the headband 12a, the top part of the visor member 11g and the spacer member 12b. The structure of the headband construction 12 is defined by two parameters "x" and "y", wherein x is the angle the visor member 11 is declined from the vertical (or the plane of the face), measured is degrees, and y is the distance the top edge of the visor member 11 is from the forehead of the wearer, measured in millimeters.

The visor member 11 is spaced from the forehead in order at the facial features such as the nose and the eyebrows are accommodated. The visor member 11 may be angled towards the plane of the face. Angling the visor member 11 in this manner provides an eye shade 10 that is distinctive i appearance and which offers the benefit of increasing the shading of the eyes from a light source such as the sun.

Figure 4:
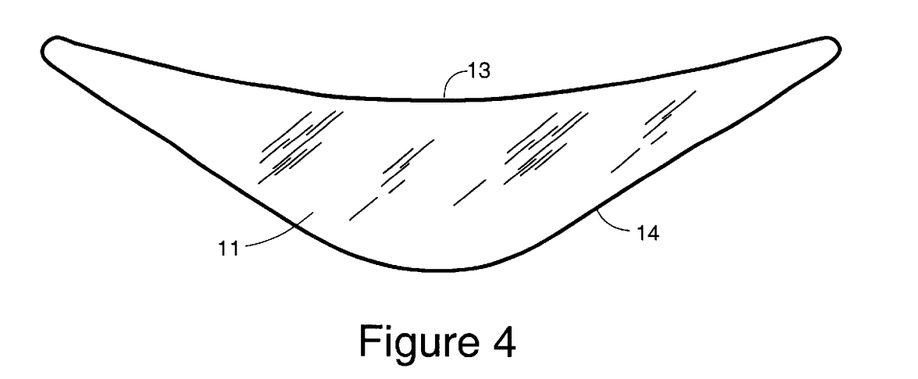
FIG. 4 is a plane development of the visor part of the eye shade.
Figure 5:
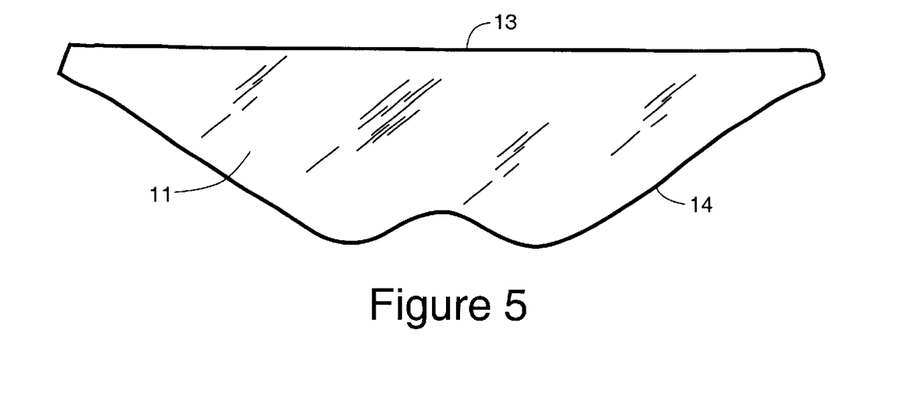
FIG. 5 is a plane development of the visor part of an alternative arrangement of the eye shade.

FIG. 4 depicts a plane of development view of an exemplary visor member 11. There are two curved edges to the visor member 11, top edge 13 and bottom edge 14. In the eye shade 10, the angle of declination, x, of the visor member 11, is dependent on the degree of curvature of the top edge 13. However, the degree of curvature and the shape of the bottom edge 14 are not essential features of the invention and are variable to suit the requirements of the eye shade 10. FIG. 5 illustrates a possible alternative shape for the visor member 11.

Figure 6:
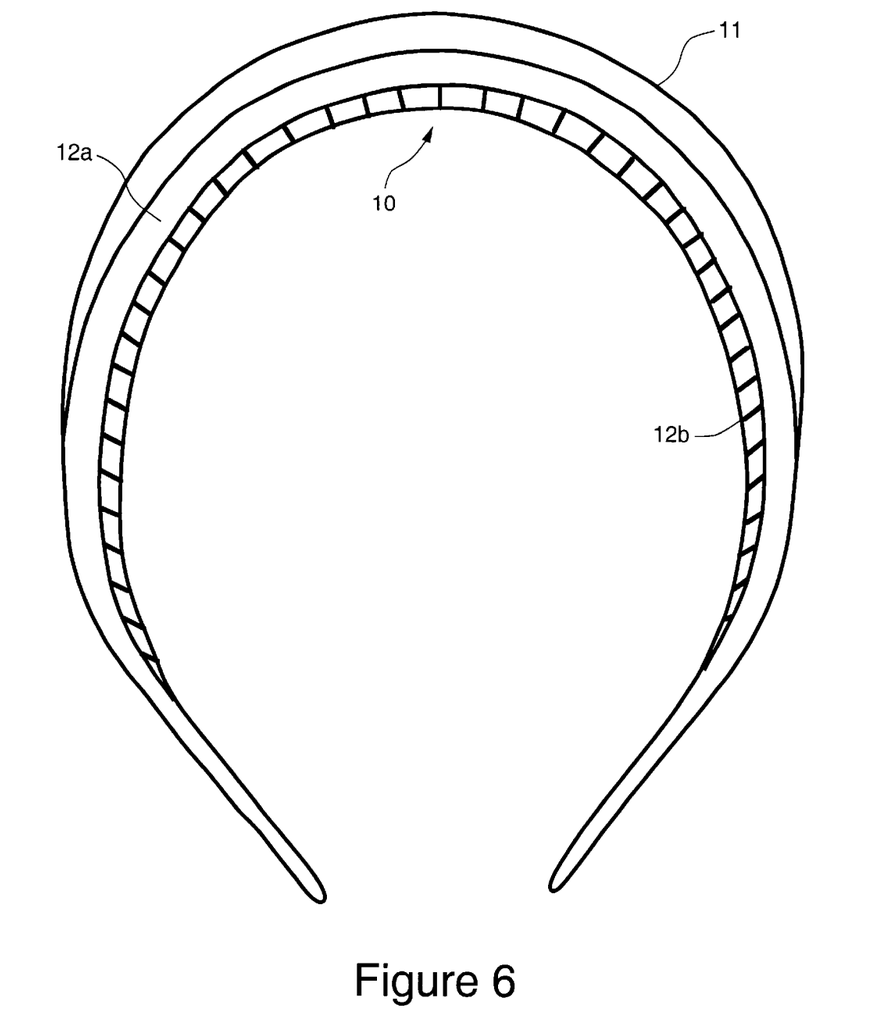
FIG. 6 is a plan view of the eye shade as seen from above the plane of the headband.

FIG. 6 shows a view of the eye shade 10 of FIG. 1 as seen from above the plane of the headband construction 12. This visor member 11 projects only slightly away from the headband construction 12 due to the small angle of declination the visor member 11 is from the vertical.

Figure 7:
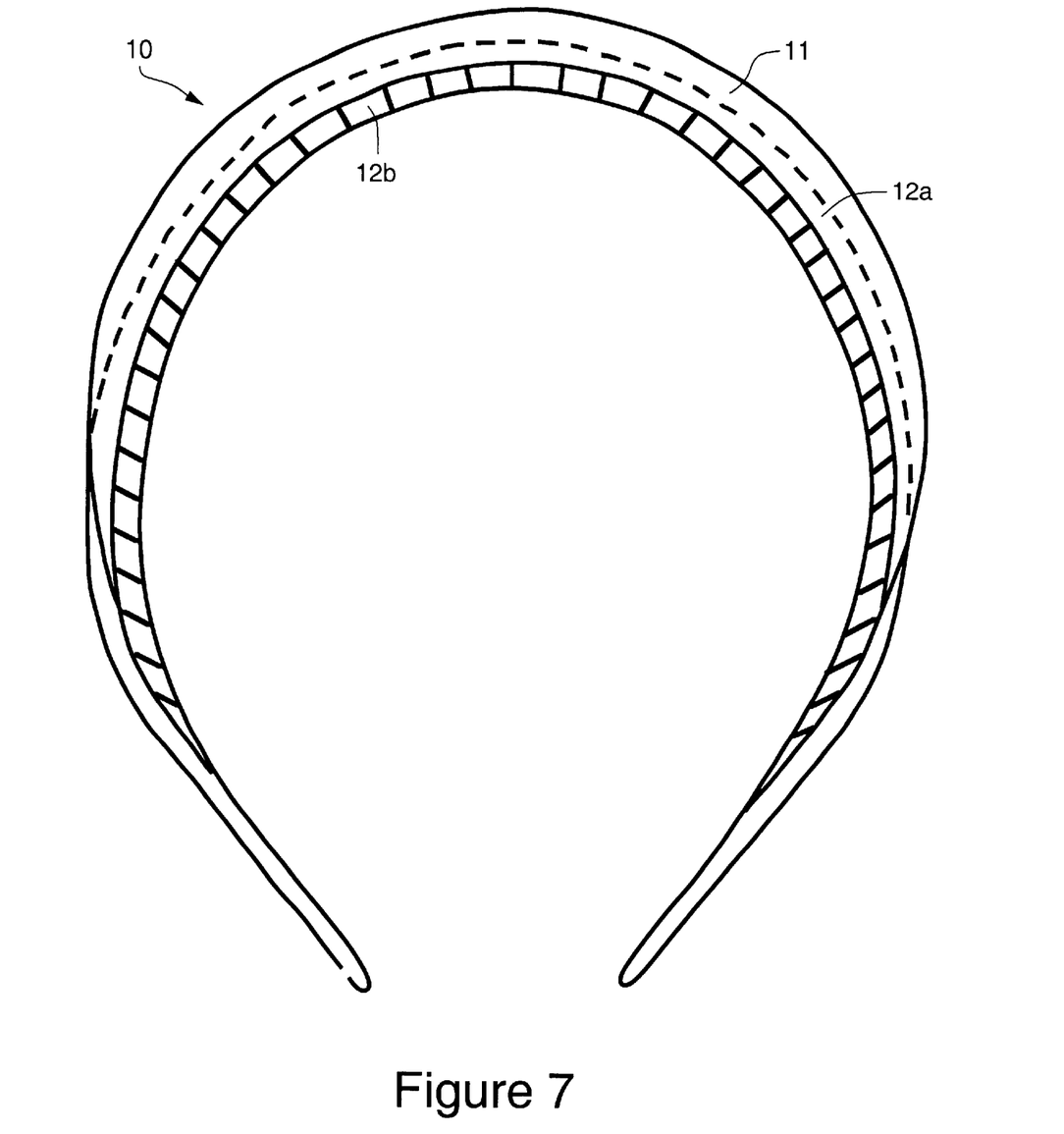
FIG. 7 is a plan view of the eye shade as seen from below the plane of the headband.

FIG. 7 depicts a view of eye shade 10 of FIG. 1 as seen from below the plane of the headband construction 12. As with FIG. 4, it can clearly be seen that the visor member 11 projects only slightly away from the headband 12, and this provides for a greater degree of shading of the eyes of the wearer.

Different arrangements of the eye shade 10 shown in FIG. 1 may be constructed to satisfy the different requirements imposed by, for example, the environment. Hence, the visor member 11 may be incorporated in the headband construction 12 in such a manner so that it is angled relative to the plane of the face from −10° to 15°.

Of the possible arrangements of the eye shade 10 shows in FIG. 1, examples of particularly preferred embodiments are described in more detail below.

The visor member 11 of the eye shade 10 comprises a top edge 13 and a bottom edge 14. The location of the top edge 12 of the visor member 11 in relation to the forehead of the wearer may play an important part in establishing the optimum correlation between shading effectiveness and comfort. Preferably, the top edge 12 of the visor member 11 is spaced from 10 to 30 mm, move preferably 15 to 25 mm, from the wearer's forehead. In one particular arrangement the eye shade 10 is configured such that the space between the forehead and the top edge 13 of the visor member 11 is about 20 mm which is believed to be the most comfortable configuration for the average adult wearer and which allows the wearer to wear glasses in conjunction with the eye shade 10.

A further feature of the visor member 11 is the angle of the surface of the visor member 11 relative to the plane of the face. This downward angle lies preferably from 0° to 15°, more preferably from 0° to 10° most preferably about 2° from the plane of the face. It is at this angle that the wearer is shaded from the sun most effectively, and, if appropriate allows spectacles to worn. De to the "wrap-around" nature of the visor member 11, the wearer is shaded from both direct sunlight and reflected glare.

In a further alternative arrangement of this embodiment, the key structural features of the invention may be such that they ideally suit a wearer who does not use spectacles. In this arrangement, the top edge 14 of the visor member 11 is spaced preferably from 2 to 25 mm and more preferably from 2 to 10 mm from the wearer's forehead. In one particularly preferred arrangement, the eye shade 10 is configured such that the space between the forehead and the top edge of the visor member 11 is about 15 mm which is believed to be a comfortable configuration for an average adult wearer who does not need to wear spectacles.

A further feature of this arrangement of the eye shade 10 is the angle of the surface of the visor member 11 to the plane of the face. This downward angle lies preferably from 0° to 15° and most preferably about 10 degrees from the plane of the face. It is at this angle that the wearer is shaded from the sun most effectively, should he not need the use of spectacles. As with the previous arrangement of this embodiment, due to the "wrap-around" nature of the visor member 11, the wearer is shaded from both direct sunlight and reflected glare.

In order to enhance of the degree of shading possible, especially from sunlight reflected upwards from a surface such as water, snow or a road, the visor member 11 may be angled towards the plane of the face. The negative angle lines from −10° to 0° and preferably from −7° to 0°.

The visor member 11 may be fabricated from any suitable transparent, lightweight and flexible material. The visor member 11 is preferably fabricated from a plastic material. The plastic material may be treated, preferably prior to being fashioned into the required shape, with one or more protective substances that reflect absorb or reflect and absorb the sun's radiation. This not only allows shading from the sun but also reflection or absorption of harmful solar radiation.

In order for the eye shade 10 to be retained in the required position, one embodiment of the present invention incorporates the visor member 11 in to a headband construction 12. In a particular arrangement of this embodiment, the headband construction 12 may be in the form of an arc which does not rely on the attachment of its two ends, which would form a full band around the head, but rather on the grip the arc-like arrangement has on the head of the wearer. The headband construction 12 may be connected from more than one layer. The innermost layer, or spacer member 12b, is preferably fabricated from any suitable material, such as a foamed plastic material.

In one arrangement of this embodiment, the two ends of the headband construction 12 may be connected with an appropriate means of attachment at the back of the head, thus further securing the eye shade 10 around the head. In addition, in alternative arrangement, the headband construction 12 may be manufactured from a material that may be elastic and as such form a complete circle around the head.

In addition, the headband construction 12 may itself be comprised of a plurality of layers of material. Preferably, a duality of layers of any suitable material, sandwich the top part of the visor member thus forming a laminate structure designed for strength and durability. The visor member 11 may be preference be sewn into the laminated headband.

The contact surfaces of the layers in the laminated headband construction 12 may be fixed using any appropriate means, such as double-sided adhesive tape, adhesive, screws, lugs, studs and soap-fit clips. This means provides strength in the headband construction 12 and also a suitable degree of flexure-resistance.

Figure 8:
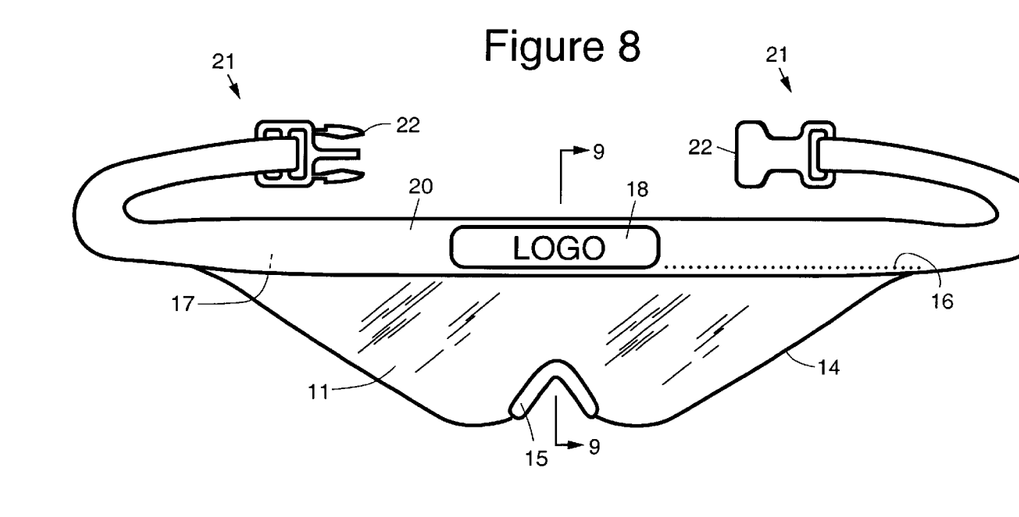
FIG. 8 is a front perspective view of another preferred embodiment of the present eye shade.

Referring now to FIG. 8, it is a from perspective view of an another preferred embodiment of the eye shade 20. This embodiment of the eye shade 10 has the visor member 11 preferably configured with a resilient protective nosepiece 15 upon which the eye shade may rest on a wearer's nose without causing discomfort. This embodiment has a headband construction 12 that comprises a fabric material 20 that wraps around the top edge 13 of the visor member 11 and is sewn 16 or adhesively attached 17 to the visor member 11.

The headband construction 12 may have a logo 16 or other advertisement 18 disposed on an exposed surface thereof. The logo 18 of advertisement may be embroidered, stitched or otherwise affixed to the exposed surface of the headband construction 12. The headband construction 12 is flexible, particularly beyond the respective ends of the visor member 11 so that it may be wrapped around the wearer's head. The distal ends of the headband construction 12 may be provided with attachable ends 21 that may be secured together using various types of fasteners 22.

Figure 9:
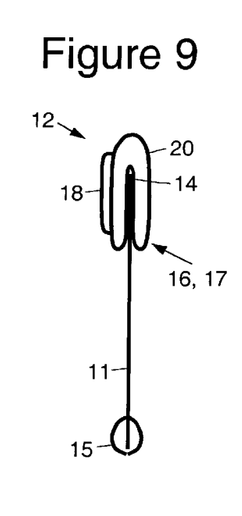
FIG. 9 is a cross sectional view of the eye shade shown in FIG. 8 taken along the line 9—9.

FIG. 9 is a cross sectional view of the eye shade 10 shown in FIG. 8 taken along the line 9—9. The resilient protective nosepiece 15 has a slit in it that allows it to slide onto and be affixed to the visor member 11. The nose piece 15 may be adhesively secured to the visor member 11 if desired. The fabric material 20 is shown wrapped around the top edge 14 of the visor member 11 and is sewn 16 or adhesively attached 17 thereto.

Figure 10:
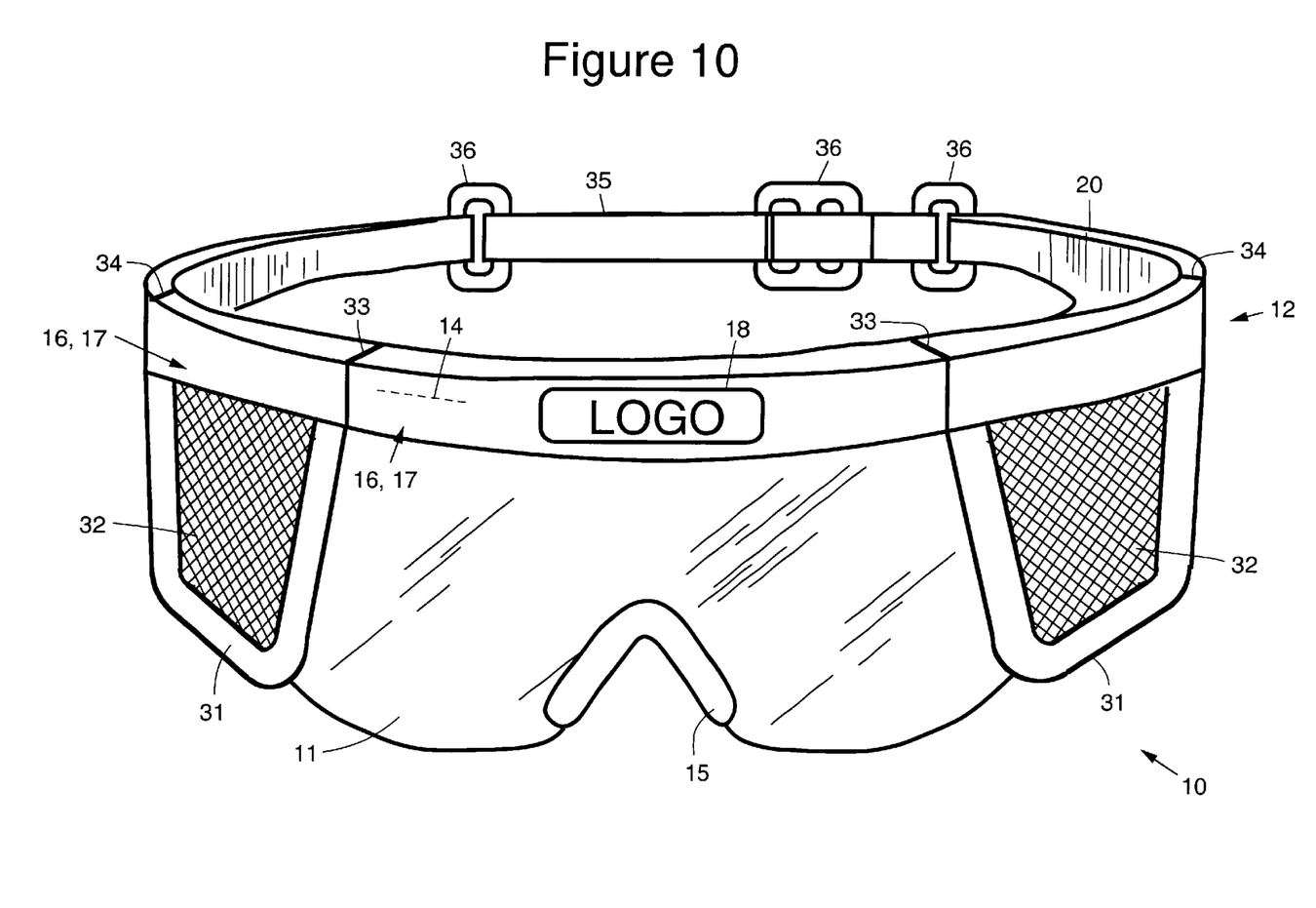
FIG. 10 is a front perspective view of an exemplary foldable eye shade in accordance with the principles of the present invention.

Referring now to FIG. 10, it shows a front perspective view of an exemplary foldable eye shade 10 in accordance with the principles of the present invention. In this embodiment of the holder eye shade 10, the visor member 11 is preferably configured with a resilient protective nosepiece 15 and distal ends of the visor member 11 are secured to vented end members 31. The vented end members 31 are preferably made of a resilient, flexible material. The vented end members 31 have a central mesh 32 or screen that permits ventilation through the sides of the eye shade 10.

The headband construction 12 wraps around the top edge 14 of the visor member 11 (shown using a dashed line) and is sewn 16 or adhesively attached 17 to the visor member 11 and the vented end members 31. The headband construction 12 and the vented end members 31 are bendable or foldable particularly beyond the respective distal ends of the visor member 11. This is illustrated by folds 33 adjacent the respective distal ends of the visor member 11.

The headband construction 12 is also flexible beyond the respective ends of the vented end members 31. This is illustrated by folds 34 adjacent the respective distal ends of the vented end members 31. Thus, the eye shade 10 is foldable between the visor member 11 and the respective vented end members 31 and at the respective ends of the vented end members 31.

The headband construction 12 may be attached to an adjustable or stretchable member 35 or material 35 to allow the eye shade 10 to be slipped over the top portion of the head of the wearer. The headband construction 12 may be attached to the adjustable or stretchable member 35 by securing their respective ends to connectors 36 such as by sewing, for example, that allow adjustment of the length of the adjustable or stretchable member 35. Alternatively, the headband construction 12 may be provided with attachable ends 21 that are secured together using fasteners 22 of various kinds in the manner shown in FIG. 8, for example, and that permit length adjustment of the headband construction 12.

Figure 11:
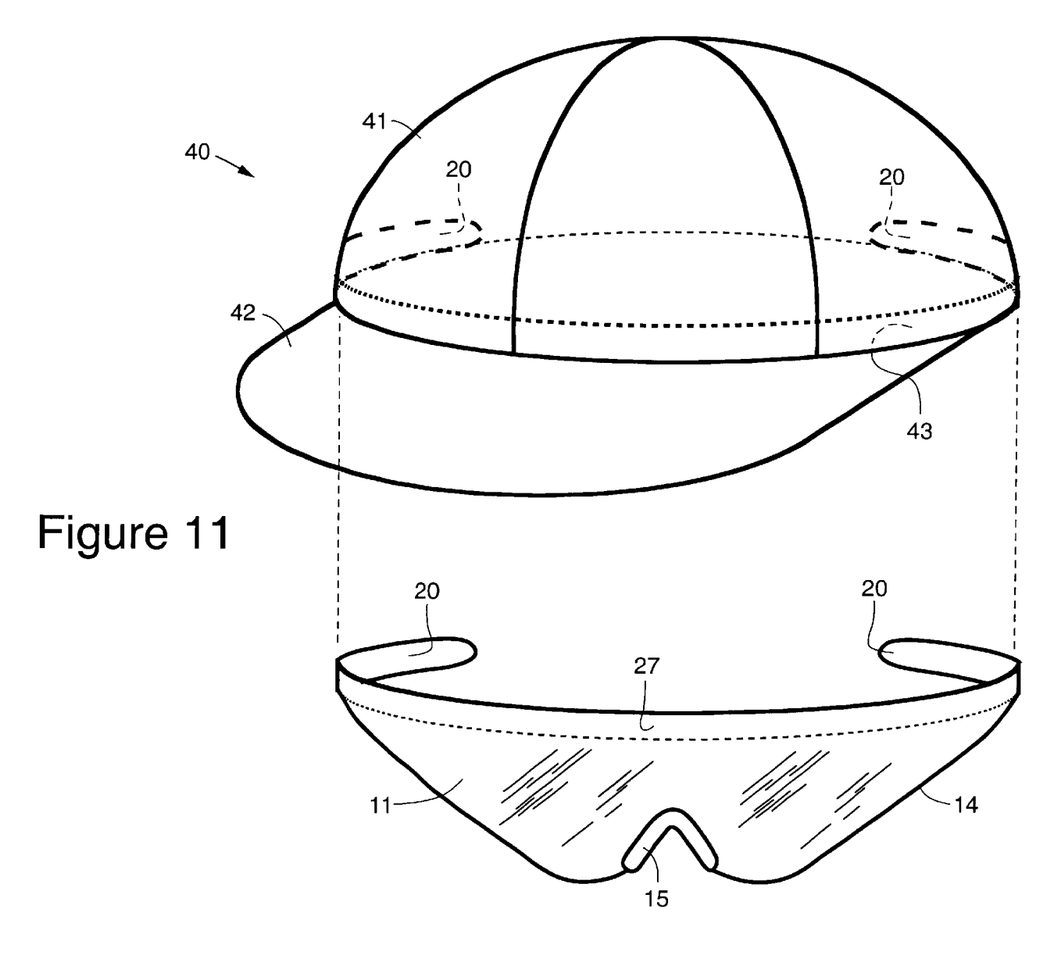
FIG. 11 is an exploded view of a hat embodying an eye shade in accordance with the principles of the present invention.

FIG. 11 is an exploded view of a hat 40 embodying an eye shade 10 in accordance with the principles of the present invention. The hat 40 comprises a body 41 having a bill 42 that generally shields the face of a wearer from the sun. The eye shade 10 has a visor member 11 generally configured in the manner shown in FIGS. 5 or 8, for example. The visor member 11 has an adhesive layer 27 applied to its outer surface (the surface facing away from the face, and the inner side of the visor member 11 which comes in contact with the forehead of the wearer has a foam or fabric material 20 attached thereto. The foam or fabric material 20 minimizes abrasion of the forehead by the eye shade 10.

The eye shape 10 is inserted into the inner portion of the hat 40 so that the adhesive layer 27 on the outer surface of the vision member 11 contacts the inner surface of the body 41 of the hat 40. The adhesive layer 27 secures the eye shape 10 to the hat 40. Alternatively, the eye shade 10 may be secured to the hat 40 by sewing the visor member 11 to the body of the hat 40, in the manner described with reference to FIG. 8, for example.

It is also to be understood that each feature of the various eye shade 10s disclosed in the specification (which term includes the claims) and/or shown in the drawings may be incorporated in the invention independently of other disclosed and/or illustrated features.

Thus, improved eye shades have been disclosed. It is to be understood that the described embodiments are merely illustrative of some of the many specific embodiments that represent application of the principles of the present invention. Clearly, numerous and other arrangement scan be readily devised by those skilled in the art without departing from the scope of the invention.

What is claimed is:

1. An eye shade comprising:
   a transparent visor member;
   a layer of foam material disposed adjacent to the transparent visor member that wraps around the transparent visor member; and
   a fabric headband that wraps around the layer of foam material and the transparent visor member that is sewn to the transparent visor member.

2. The eye shade recited in claim 1 wherein the fabric headband and the layer of foam material have a combined thickness that spaces the transparent visor member away from a wearer's forehead from 2 to 25 millimeters when the eye shade is worn.

3. The eye shade recited in claim 1 wherein the visor member is disposed at an angle of from −10 degrees to +15 degrees relative to a vertical plane in front of a wearer's face.

4. The eye shade recited in claim 1 wherein the headband comprises fastening means that are operative to secure the headband around the wearer's head when the eye shade is worn.

5. The eye shade recited in claim 1 wherein the wherein the visor member comprises flexible plastic material.

6. The eye shade recited in claim 1 further comprising a resilient protective nosepiece disposed on a bottom edge of the transparent visor member.

7. The eye shade recited in claim 1 wherein the headband is foldable beyond respective distal ends of the visor member.

8. The eye shade recited in claim 7 wherein distal ends of the visor member comprise vented end members.

9. The eye shade recited in claim 8 wherein the vented end members have a central mesh that permits ventilation through sides thereof.

10. The eye shade recited in claim 1 wherein the visor member further comprises a spacer disposed adjacent a side that contacts a wearer's forehead.

11. An eye shade comprising:
    a transparent visor member;
    a resilient protective nosepiece disposed on a bottom edge of the transparent visor member;
    a layer of foam material that wraps around the transparent visor member; and
    a fabric headband that wraps around the layer of foam material and the transparent visor and that is sewn to the transparent visor member.

12. The eye shade recited in claim 11 wherein the fabric headband and the layer of foam material have a combined thickness that spaces the transparent visor member away from a wear's forehead from 2 to 25 millimeters when the eye shade is worn.

13. The eye shade recited in claim 11 wherein the visor member is disposed at an angle of from −10 degrees to +15 degrees relative to a vertical plane in front of a wearer's face.

14. The eye shade recited in claim 11 wherein the headband comprises fastening means that are operative to secure the headband around the wearer's head when the eye shade is worn.

15. The eye shade recited in claim 11 wherein the wherein the visor member comprises flexible plastic material.

16. The eye shade recited in claim 11 wherein the layer of foam material wraps around the transparent visor member.

17. The eye shade recited in claim 11 wherein the headband is foldable beyond respective distal ends of the visor member.

18. The eye shade recited in claim 11 wherein distal ends of the visor member comprise vented end members.

19. The eye shade recited in claim 15 wherein the vented end members have a central mesh that permits ventilation through sides thereof.

20. An eye shade comprising:
- a transparent visor member that is disposed at an angle of from −10 degrees to +15 degrees relative to a vertical plane in front of a wearer's face;
- a layer of foam material disposed adjacent to the transparent visor member; and
- a fabric headband that wraps around the layer of foam material and the transparent visor member that is sewn to the transparent visor member.

21. The eye shade recited in claim 20 wherein the fabric headband and the layer of foam material have a combined thickness that spaces the transparent visor member away from a wearer's forehead from 2 to 25 millimeters when the eye shade is worn.

22. The eye shade recited in claim 20 wherein the visor member is disposed at an angle of from −10 degrees to +15 degrees relative to a vertical plane in front of a wearer's face.

23. The eye shade recited in claim 20 wherein the headband comprises fastening means that are operative to secure the headband around the wearer's head when the eye shade is worn.

24. The eye shade recited in claim 20 further comprising a resilient protective nosepiece disposed on a bottom edge of the transparent visor member.

\* \* \* \* \*